(12) United States Patent
Biatry et al.

(10) Patent No.: US 7,560,493 B2
(45) Date of Patent: *Jul. 14, 2009

(54) COSMETIC AND/OR DERMATOLOGICAL COMPOSITION CONTAINING AT LEAST ONE OXIDATION-SENSITIVE HYDROPHILIC ACTIVE PRINCIPLE AND AT LEAST ONE N-VINYLIMIDAZOLE POLYMER OR COPOLYMER

(75) Inventors: Bruno Biatry, Vincennes (FR); Eric Lheureux, Montgerno (FR)

(73) Assignee: L'Oreal, Paris (FR)

( * ) Notice: Subject to any disclaimer, the term of this patent is extended or adjusted under 35 U.S.C. 154(b) by 439 days.

This patent is subject to a terminal disclaimer.

(21) Appl. No.: 10/304,860

(22) Filed: Nov. 27, 2002

(65) Prior Publication Data

US 2003/0143275 A1    Jul. 31, 2003

(30) Foreign Application Priority Data

Nov. 28, 2001 (FR) .................................. 01 15375

(51) Int. Cl.
*A61K 47/34* (2006.01)

(52) U.S. Cl. .................... 514/772.7; 424/400; 514/772; 514/772.2; 514/772.4

(58) Field of Classification Search ........................ None
See application file for complete search history.

(56) References Cited

U.S. PATENT DOCUMENTS

| | | | |
|---|---|---|---|
| 3,242,051 A | 3/1966 | Hiestand et al. | |
| 3,531,427 A | 9/1970 | Kervenski et al. | |
| 3,714,065 A | 1/1973 | Kitajima et al. | |
| 4,229,430 A * | 10/1980 | Fahim et al. | 424/49 |
| 4,465,629 A | 8/1984 | Maughan | |
| 5,032,384 A | 7/1991 | Yeh et al. | |
| 5,081,111 A | 1/1992 | Akimoto et al. | |
| 5,607,692 A | 3/1997 | Ribier et al. | |
| 5,667,791 A | 9/1997 | Hersh et al. | |
| 5,703,041 A | 12/1997 | Afriat et al. | |
| 5,801,192 A * | 9/1998 | Dumas et al. | 514/474 |
| 5,882,658 A | 3/1999 | Simon et al. | |
| 5,891,452 A | 4/1999 | Sebillote-Arnaud et al. | |
| 5,945,032 A * | 8/1999 | Breitenbach et al. | 252/186.29 |
| 6,008,274 A | 12/1999 | Meyer et al. | |
| 6,024,942 A | 2/2000 | Tanner et al. | |
| 6,068,847 A | 5/2000 | Aleles et al. | |
| 6,103,267 A | 8/2000 | Mitchnick et al. | |
| 6,126,926 A | 10/2000 | Tanaka et al. | |
| 6,162,448 A * | 12/2000 | Nguyen et al. | 424/401 |
| 6,191,188 B1 * | 2/2001 | Hossel et al. | 523/105 |
| 6,232,373 B1 | 5/2001 | Lappas et al. | |
| 6,391,292 B1 | 5/2002 | Samain et al. | |
| 6,395,285 B1 * | 5/2002 | Lorant | 424/401 |
| 6,468,552 B1 * | 10/2002 | Stahl et al. | 424/401 |
| 6,531,160 B2 | 3/2003 | Biatry et al. | |
| 6,533,823 B2 | 3/2003 | Nakashimada et al. | |
| 6,596,695 B2 | 7/2003 | Castiel et al. | |
| 6,684,530 B2 | 2/2004 | Opazo | |
| 6,764,693 B1 * | 7/2004 | Smith | 424/450 |
| 2002/0022038 A1 | 2/2002 | Biatry et al. | |
| 2003/0190335 A1 | 10/2003 | Boussouira et al. | |
| 2004/0001792 A1 | 1/2004 | Biatry | |
| 2004/0042990 A1 | 3/2004 | Biatry | |
| 2004/0047824 A1 | 3/2004 | Biatry | |
| 2004/0175342 A1 | 9/2004 | Biatry | |
| 2004/0223986 A9 | 11/2004 | Boussouira et al. | |
| 2006/0051425 A1 | 3/2006 | Kvitnitsky et al. | |

FOREIGN PATENT DOCUMENTS

| | | |
|---|---|---|
| EP | 0 282 951 | 9/1988 |
| EP | 0 380 367 | 8/1990 |
| EP | 1 133 974 | 9/2001 |

OTHER PUBLICATIONS

Sigma-Aldrich BioChemika Ultra disclosure, downloaded from the world wide web on Jul. 19, 2007.*
ACS News "Chemistry Grads Post Gains in 2005", Chemical and Engineering News, Jul. 24, 2006.*
Franchi, Jocelyne, et al., Depigmenting Effects of Calcuium D-Panthetheine S-Sulfonate on Human Melanocytes, Jun. 2000, Pigment Cell Research, vol. 13, p. 165.
Zreik, et al., Molecular Human Reproduction 1999, 5(4), 299-302.

* cited by examiner

*Primary Examiner*—Eric E. Silverman
(74) *Attorney, Agent, or Firm*—Oblon, Spivak, McClelland, Maier & Neustadt, P.C.

(57) ABSTRACT

The invention relates to a composition for topical use containing, in a physiologically acceptable medium having an aqueous phase, at least one oxidation-sensitive hydrophilic active principle and at least one non-crosslinked N-vinylimidazole polymer or copolymer, the active principle and the said polymer or copolymer both being in the aqueous phase.

14 Claims, No Drawings

US 7,560,493 B2

COSMETIC AND/OR DERMATOLOGICAL COMPOSITION CONTAINING AT LEAST ONE OXIDATION-SENSITIVE HYDROPHILIC ACTIVE PRINCIPLE AND AT LEAST ONE N-VINYLIMIDAZOLE POLYMER OR COPOLYMER

FIELD OF THE INVENTION

The present invention relates to a composition comprising at least one oxidation-sensitive hydrophilic active principle and at least one N-vinylimidazole polymer or copolymer. Preferably the composition is a cosmetic and/or dermatological composition. Also, preferably, the composition comprises a physiologically acceptable medium comprising an aqueous phase.

BACKGROUND OF THE INVENTION

It is known to introduce, into cosmetic compositions, various active principles intended to contribute specific treatments to the skin and/or hair. However, some of these active principles exhibit the disadvantage of being unstable in an aqueous medium and of easily decomposing on contact with water, in particular because of oxidation phenomena. They thus rapidly lose their activity over time and this instability conflicts with the desired effectiveness.

Attempts have thus been made for a long time to formulate ascorbic acid or vitamin C because of its numerous beneficial properties. In particular, ascorbic acid stimulates the synthesis of the connective tissue and in particular of collagen, strengthens the defenses of the cutaneous tissue against external attacks, such as ultraviolet radiation and pollution, compensates for vitamin E deficiency of the skin, depigments the skin and has a role in combatting free radicals. These last two properties make it an excellent candidate as cosmetic or dermatological active principle for combatting ageing of the skin or for preventing ageing of the skin. Unfortunately, because of its chemical structure (of α-ketolactone), ascorbic acid is highly sensitive to certain environmental parameters and in particular to oxidation phenomena. There thus ensues rapid decomposition of formulated ascorbic acid in the presence of these parameters and in particular in the presence of oxygen, light or metal ions, as a function of the temperature or under certain pH conditions (Pharm. Acta. Helv., 1969, 44, 611-667; STP Pharma, 1985, 4, 281-286).

Several solutions have thus been envisaged in the prior art for reducing and/or slowing down the decomposition of ascorbic acid.

Provision has thus been made to use ascorbic acid in the form of a chemical derivative (magnesium ascorbyl phosphate or esters of fatty acids and ascorbic acid), but the bioavailability of these derivatives is very low (J. Am. Acad. Dermatol., 1996, 34, 29-33).

The instability of ascorbic acid with respect to oxygen can be improved by using specific packagings, such as twin compartments under an inert atmosphere, as disclosed in U.S. Pat. No. 5,935,584, or alternatively by the use of two-phase emulsions, one phase of which is composed of a dry powder comprising ascorbic acid and the second phase of which is a liquid phase. The mixing of the two phases has to be carried out at the time of use (WO 98/43598). These solutions have disadvantages with regard to the cost and the complexity of the manufacturing operations and significant restrictions with regard to use.

Another solution provided in the prior art consists in using a high concentration of glycols or polyols in order to reduce the solubility of oxygen in the formulation, thus protecting the ascorbic acid (WO 96/24325, EP 0 755 674, U.S. Pat. No. 5,981,578). The polyols can optionally be incorporated in liposomes, as disclosed in U.S. Pat. No. 6,020,367. However, these solutions exhibit the disadvantage of resulting in sticky formulations, the cosmetic quality of which is difficult to improve. Furthermore, the presence of a high concentration of these compounds can lead to phenomena of irritation.

Ascorbic acid can also be formulated in anhydrous media, such as silicones (U.S. Pat. No. 6,194,452), which are capable of creating an anhydrous barrier around ascorbic acid. A major disadvantage of such solutions results from the lack of freshness on application.

The need thus remains for a composition employable in particular in the cosmetics field, in which a hydrophilic active principle which is unstable in an oxidizing medium is stabilized, which is comfortable on application, which does not lead to any skin irritation after application and which is compatible with the constraints of an industrial implementation of its manufacturing process.

OBJECTS OF THE INVENTION

One object of the present invention is to provide a composition comprising an oxidation-sensitive active principle, which preferably exhibits good cosmetic properties, both with regard to touch and with regard to tolerance, and the preservation of which over time does not require specific precautions.

SUMMARY OF THE INVENTION

The inventors have discovered that the use of non-crosslinked N-vinylimidazole polymers or copolymers in compositions in which the aqueous phase includes an oxidation-sensitive active principle, such as ascorbic acid, makes it possible to achieve the abovementioned object.

In the prior art, some compounds having an imidazole structure have been disclosed for their stabilizing properties. Thus, in Patent Application EP 0 586 106, several imidazole-based molecules are used to stabilize certain retinoids against chemical decomposition. Furthermore, polymeric emulsifiers composed of N-vinylimidazole, of alkyl acrylates and of vinyl acetates are disclosed in U.S. Pat. No. 4,057,622. They are used for the purpose of replacing known emulsifiers in order to overcome their disadvantages, in particular with regard to smell, and to stabilize water-in-oil emulsions. Finally, N-vinylimidazole/N-vinylcaprolactam/N-vinylpyrrolidone copolymers are disclosed in U.S. Pat. No. 6,191,188. They are used in the manufacture of hair-strengthening compositions.

To the knowledge of the inventors, polymers or copolymers comprising N-vinylimidazole units have never been used in combination with hydrophilic active principles sensitive to decomposition by oxidation for the purpose of improving their stability in an aqueous medium. This is true in particular in the case of ascorbic acid.

An embodiment of the present invention is therefore a composition preferably for topical use comprising, preferably in a physiologically acceptable medium comprising an aqueous phase, at least one oxidation-sensitive hydrophilic active principle and at least one non-crosslinked N-vinylimidazole polymer or copolymer, the at least one active principle and the at least one polymer or copolymer both being present in the aqueous phase. The copolymer is generally preferably present in an amount sufficient to stabilize the oxidation-sensitive hydrophilic active principle.

The invention also relates to the use of a non-crosslinked N-vinylimidazole polymer or copolymer to stabilize an oxidation-sensitive hydrophilic active principle in an aqueous medium.

According to the invention, the term "hydrophilic active principle" is understood to mean a compound having a solubility in water of at least 0.25% at ambient temperature (25° C.).

According to the invention, the term "oxidation-sensitive hydrophilic active principle" is understood to mean any active principle of natural or synthetic origin capable of undergoing decomposition by an oxidation mechanism. This oxidation phenomenon can have several causes, in particular the presence of oxygen, of light or of metal ions, a high temperature or certain pH conditions.

Mention may be made, by way of example and without implied limitation, of: ascorbic acid and its derivatives, such as salts or esters thereof, particularly the 5,6-di-O-dimethylsilylascorbate (sold by Exsymol under the reference PRO-AA), the potassium salt of dl-α-tocopheryl dl-ascorbyl phosphate (sold by Senju Pharmaceutical under the reference SEPIVITAL EPC), magnesium ascorbyl phosphate or sodium ascorbyl phosphate (sold by Roche under the reference Stay-C 50). Mention may also be made of active principles, such as phloroglucinol and kojic acid.

Among oxidation-sensitive hydrophilic active principles, ascorbic acid is more particularly preferred.

The oxidation-sensitive hydrophilic active principle may be present in any amount, preferably that amount sufficient to bring about its desired effect(s). Examples include 0.5, 1, 5, 15 and 25 grams per 100 grams of composition.

According to the invention, the term "non-crosslinked N-vinylimidazole polymer or copolymer" is understood to mean any polymer comprising N-vinylimidazole units and not comprising a crosslinking agent. Copolymers suitable for the implementation of the invention are, for example, copolymers combining N-vinylimidazole, with N-vinylpyrrolidone and/or N-vinylcaprolactam subunits.

In an advantageous aspect of the invention, the copolymer has a molar fraction of N-vinylimidazole units of between 0.1 and 1, more preferably between 0.4 and 0.9.

According to another advantageous aspect of the invention, the molar ratio of the N-vinylimidazole unit equivalent to the oxidation-sensitive hydrophilic active principle varies between 0.004 and 16 and preferably between 0.01 and 1.

Use will preferably be made of an N-vinylimidazole/N-vinylpyrrolidone copolymer.

The weight-average molar mass of the N-vinylimidazole polymers will advantageously be between 1 000 and $1 \times 10^7$ and preferably between 5 000 and $5 \times 10^6$.

Use may be made, to this end, of the vinylpyrrolidone/vinylimidazole (50/50) copolymer having a weight-average molar mass of 1 200 000 sold under the reference LUVITEC VPI 55K72W by BASF or the vinylpyrrolidone/vinylimidazole (50/50) copolymer having a weight-average molar mass of 10 000 sold under the reference LUVITEC VPI 55K18P by BASF. The polymers or copolymers according to the invention can, for example, be prepared according to the method disclosed in Patent Application WO-97/45517.

The at least one polymer or copolymer is preferably present in the composition according to the invention in an amount sufficient to produce the desired effect, that is to say in an amount sufficient to stabilize the oxidation-sensitive hydrophilic active principle. Preferably, the at least one polymer or copolymer is present at a concentration of between 0.1 and 5% by weight with respect to the total weight of the aqueous phase and more particularly at a concentration of between 0.1 and 2% by weight with respect to the total weight of the aqueous phase, all concentrations within these ranges being specifically included as if written out. A stabilizing amount includes any amount that delays or prevents oxidation, for example at 45° C. for two months, as compared to the composition lacking the at least one polymer or copolymer.

The compositions used according to the invention are preferably intended for topical application to the skin and/or its superficial body growths and therefore preferably comprise a physiologically acceptable medium, that is to say a medium compatible with cutaneous tissues, such as the skin, scalp, eyelashes, eyebrows, hair, nails and mucous membranes. This physiologically acceptable medium preferably comprises at least one aqueous phase and optionally a physiologically acceptable organic solvent chosen, for example, from lower alcohols comprising from 1 to 8 carbon atoms and in particular from 1 to 6 carbon atoms, such as ethanol, isopropanol, propanol or butanol; polyethylene glycols having from 6 to 80 ethylene oxide units; or polyols, such as propylene glycol, isoprene glycol, butylene glycol, glycerol or sorbitol.

When the physiologically acceptable medium is an aqueous medium, it generally has a pH which is compatible with the skin, preferably ranging from 3 to 9 and better still from 3.5 to 7.5.

The compositions according to the invention can be provided in any form, including any pharmaceutical dosage form used conventionally for topical application and in particular in the form of aqueous or aqueous/alcoholic solutions, of oil-in-water (O/W) or water-in-oil (W/O) or multiple (triple: W/O/W or O/W/O) emulsions, of aqueous gels or of dispersions of a fatty phase in an aqueous phase using spherules, it being possible for these spherules to be polymeric nanoparticles, such as nanospheres and nanocapsules, or lipid vesicles of ionic and/or nonionic type (liposomes, niosomes or oleosomes). These compositions can be prepared according to the usual methods by one of ordinary skill in view of this disclosure.

In addition, the compositions according to the invention can be more or less fluid and can have the appearance of a white or coloured cream, of an ointment, of a milk, of a lotion, of a serum, of a paste or of a foam. They can optionally be applied to the skin in the form of an aerosol. They can also be provided in a solid form, for example in the form of a stick.

When the compositions according to the invention comprise an oily phase, the latter preferably comprises at least one oil. It can additionally comprise other fatty substances.

Mention may be made, as oils which can be used in the composition of the invention, of, for example:

hydrocarbonaceous oils of animal origin, such as perhydrosqualene;

hydrocarbonaceous oils of vegetable origin, such as liquid triglycerides of fatty acids comprising from 4 to 10 carbon atoms, such as triglycerides of heptanoic acid or octanoic acid, or alternatively, for example, sunflower, maize, soybean, gourd, grape seed, sesame, hazelnut, apricot, macadamia, arara, castor or avocado oils, triglycerides of caprylic/capric acids, such as those sold by Stéarineries Dubois or those sold under the names Miglyol 810, 812 and 818 by Dynamit Nobel, jojoba oil, or karite butter oil;

synthetic esters and ethers, in particular of fatty acids, such as the oils of formulae $R^1COOR^2$ and $R^1OR^2$ in which $R^1$ represents the residue of a fatty acid comprising from 8 to 29 carbon atoms and $R^2$ represents a branched or unbranched hydrocarbonaceous chain comprising from 3 to 30 carbon atoms, such as, for example, purcellin oil, isononyl isononanoate, isopropyl myristate, 2-ethylhexyl palmitate, 2-octyldodecyl stearate, 2-octyldodecyl erucate or isostearyl isostearate; hydroxylated esters, such as isostearyl lactate, octyl hydroxystearate, octyldodecyl hydroxystearate, diisostearyl malate, triisocetyl citrate or heptanoates, octanoates or decanoates of fatty alcohols; polyol esters, such as propylene glycol dioctanoate, neopentyl glycol diheptanoate and diethylene glycol diisononanoate; and pentaerythritol esters, such as pentaerythrityl tetraisostearate;

linear or branched hydrocarbons of mineral or synthetic origin, such as volatile or nonvolatile liquid paraffins and their derivatives, liquid petrolatum, polydecenes or hydrogenated polyisobutene, such as parleam oil;

fatty alcohols having from 8 to 26 carbon atoms, such as cetyl alcohol, stearyl alcohol and their mixture (cetearyl alcohol), octyldodecanol, 2-butyloctanol, 2-hexyldecanol, 2-undecylpentadecanol, oleyl alcohol or linoleyl alcohol;

partially hydrocarbon-comprising and/or silicone-comprising fluorinated oils, such as those disclosed in the document JP-A-2-295912;

silicone oils, such as volatile or nonvolatile polymethylsiloxanes (PDMS) comprising a linear or cyclic silicone chain which are liquid or pasty at ambient temperature, in particular cyclopolydimethylsiloxanes (cyclomethicones), such as cyclohexasiloxane; polydimethylsiloxanes comprising pendent alkyl, alkoxy or phenyl groups or alkyl, alkoxy or phenyl groups at the end of the silicone chain, which groups have from 2 to 24 carbon atoms; or phenylated silicones, such as phenyl trimethicones, phenyl dimethicones, phenyltrimethyl-siloxydiphenylsiloxanes, diphenyl dimethicones, diphenylmethyldiphenyl-trisiloxanes, (2-phenylethyl) trimethylsiloxysilicates and polymethylphenylsiloxanes;

their mixtures.

The term "hydrocarbonaceous oil" is understood to mean, in the list of the oils mentioned above, any oil predominantly comprising carbon and hydrogen atoms and optionally ester, ether, fluorinated, carboxylic acid and/or alcohol groups.

The other fatty substances which can be present in the oily phase are, for example, fatty acids comprising from 8 to 30 carbon atoms, such as stearic acid, lauric acid, palmitic acid and oleic acid; waxes, such as lanolin, beeswax, carnauba or candelilla wax, paraffin or lignite waxes or microcrystalline waxes, ceresin or ozokerite, or synthetic waxes, such as polyethylene waxes or Fischer-Tropsch waxes; silicone resins, such as trifluoromethyl $C_{1-4}$ alkyl dimethicone and trifluoropropyl dimethicone; and silicone elastomers, such as the products sold under the names "KSG" by Shin-Etsu, under the names "Trefil", "BY29" or "EPSX" by Dow Corning or under the names "Gransil" by Grant Industries.

These fatty substances can be chosen in a way varied by a person skilled in the art in order to prepare a composition having the desired properties, for example of consistency or of texture.

According to a specific preferred embodiment of the invention, the composition according to the invention is a water-in-oil (W/O) or oil-in-water (O/W) emulsion. The proportion of the oily phase in the emulsion can range from 5 to 80% by weight and preferably from 5 to 50% by weight with respect to the total weight of the composition.

The invention emulsions generally preferably comprise at least one emulsifier chosen from amphoteric, anionic, cationic or nonionic emulsifiers, used alone or as a mixture, and optionally a coemulsifier. The emulsifiers are appropriately chosen according to the emulsion to be obtained (W/O or O/W). The emulsifier and the coemulsifier are generally present in the composition in a proportion ranging from 0.3 to 30% by weight and preferably from 0.5 to. 20% by weight with respect to the total weight of the composition.

Mention may be made, for the W/O emulsions, for example, as emulsifiers, of dimethicone copolyols, such as the mixture of cyclomethicone and of dimethicone copolyol sold under the name "DC 5225 C" by Dow Corning, and alkyl dimethicone copolyols, such as the laurylmethicone copolyol sold under the name "Dow Corning 5200 Formulation Aid" by Dow Corning and the cetyl dimethicone copolyol sold under the name Abil EM $_{90}{}^{R}$ by Goldschmidt. Use may also be made, as surfactant of W/O emulsions, of a crosslinked solid organopolysiloxane elastomer comprising at least one oxyalkylenated group, such as those obtained according to the procedure of Examples 3, 4 and 8 of the document U.S. Pat. No. 5,412,004 and the examples of the document U.S. Pat. No. 5,811,487, in particular the product of Example 3 (synthetic example) of U.S. Pat. No. 5,412,004, and such as that sold under the reference KSG 21 by Shin Etsu. Use may also be made, as emulsifier, of a polyolefin-derived oligomer or polymer comprising a succinic ending; the latter is preferably a polyolefin comprising an esterified or amidated succinic ending or a salt of such a polyolefin and in particular polyisobutylene comprising an esterified or amidated succinic ending such as the products sold under the names L5603 and L2721 and OS131769 by Lubrizol.

Mention may be made, for the O/W emulsions, for example, as emulsifiers, of nonionic emulsifiers, such as esters of fatty acids and of glycerol which are oxyalkylenated (more particularly polyoxyethylenated); esters of fatty acids and of sorbitan which are oxyalkylenated; esters of fatty acids which are oxyalkylenated (oxyethylenated and/or oxypropylenated); ethers of fatty alcohols which are oxyethylenated (oxyethylenated and/or oxypropylenated); sugar esters, such as sucrose stearate; and their mixtures, such as the mixture of glyceryl stearate and of PEG-40 stearate.

According to another embodiment of the invention, the invention composition may additionally comprise at least one active principle (in addition to and different from the oxidation-sensitive hydrophilic active principle) chosen from desquamating agents capable of acting either by promoting exfoliation or on the enzymes involved in the desquamation or the decomposition of corneodesmosomes, moisturizing agents, depigmenting or propigmenting agents, antiglycation agents, NO-synthase inhibitors, 5α-reductase inhibitors, lysyl and/or prolyl hydroxylase inhibitors, agents which stimulate the synthesis of dermal or epidermal macromolecules and/or which prevent their decomposition, agents which stimulate the proliferation of fibroblasts or keratinocytes and/or the differentiation of keratinocytes, muscle relaxants, antimicrobial agents, tightening agents, agents for combating pollution or free radicals, anti-inflammatory agents, lipolytic active principles or active principles which have a favourable effect, directly or indirectly, on decreasing adipose tissue, agents which act on the microcirculation, and agents which act on the energy metabolism of cells.

The composition of the invention can also comprise adjuvants known in the cosmetics or dermatological field, such as hydrophilic or lipophilic gelling agents, preservatives, solvents, fragrances, fillers, UV screening agents, bactericides, odour absorbers, colouring materials, plant extracts or salts. The amounts of these various adjuvants are those generally used in the field under consideration, for example from 0.01 to 20% of the total weight of the composition. These adjuvants, depending on their nature, can be introduced into the fatty phase, into the aqueous phase and/or into the lipid spherules.

Mention may be made, as fillers which can be used in the composition of the invention, for example, of, pigments, silica powder; talc; particles of polyamide and in particular those sold under the name Orgasol by Atochem; polyethylene powders; microspheres based on acrylic copolymers, such as those made of ethylene glycol dimethacrylate/lauryl methacrylate copolymer which are sold by Dow Corning under the name Polytrap; expanded powders, such as hollow microspheres and in particular the microspheres sold under the name Expancel by Kemanord Plast or under the name Micropearl F 80 ED by Matsumoto; silicone resin microbeads, such as those sold under the name Tospearl by Toshiba Silicone; and their mixtures. These fillers can be present in amounts ranging from 0 to 20% by weight and preferably from 1 to 10% by weight with respect to the total weight of the composition.

According to a preferred embodiment, the compositions in accordance with the invention can additionally comprise at least one organic photoprotective agent and/or at least one inorganic photoprotective agent which is active in the UV-A and/or UV-B regions (absorbers), and which are soluble in water or in fats or else are insoluble in the cosmetic solvents commonly used.

The organic photoprotective agents may be chosen in particular from anthranilates; cinnamic derivatives; dibenzoylmethane derivatives; salicylic derivatives; camphor derivatives; triazine derivatives, such as those disclosed in patent applications U.S. Pat. No. 4,367,390, EP 863 145, EP 517 104, EP 570 838, EP 796 851, EP 775 698, EP 878 469, EP 933 376, EP 507 691, EP 507 692, EP 790 243 and EP 944 624; benzophenone derivatives; β,β-diphenylacrylate derivatives; benzotriazole derivatives; benzalmalonate derivatives; benzimidazole derivatives; imidazolines; bisbenzoazolyl derivatives as disclosed in Patents EP 669 323 and U.S. Pat. No. 2,463,264; p-aminobenzoic acid (PABA) derivatives; methylenebis(hydroxyphenylbenzotriazole) derivatives as disclosed in Applications U.S. Pat. No. 5,237,071, U.S. Pat. No. 5,166,355, GB 2 303 549, DE 197 26 184 and EP 893 119; screening polymers and screening silicones, such as those disclosed in particular in Application WO 93/04665; dimers derived from α-alkylstyrene, such as those disclosed in Patent Application DE 198 55 649; 4,4-diarylbutadienes as disclosed in Applications EP 0 967 200, DE 197 46 654, DE 197 55 649, EP-A-1 008 586, EP 1 133 980 and EP 133 981; and their mixtures.

By way of illustration, mention may be made, as photoprotective agents which are active in the UV-A and/or UV-B regions, denoted below under their INCI names, of:

p-aminobenzoic acid (PABA) derivatives, in particular PABA, ethyl PABA, ethyl dihydroxypropyl PABA, ethylhexyl dimethyl PABA (sold in particular under the name "Escalol 507" by ISP), glyceryl PABA or PEG-25 PABA (sold under the name "Uvinul P25" by BASF), salicylic derivatives, in particular homosalate (sold under the name "Eusolex HMS" by Rona/EM Industries), ethylhexyl salicylate (sold under the name "Neo Heliopan OS" by Haarmann and Reimer), dipropylene glycol salicylate (sold under the name "Dipsal" by Scher), or TEA salicylate (sold under the name "Neo Heliopan TS" by Haarmann and Reimer), dibenzoylmethane derivatives, in particular butyl methoxydibenzoylmethane (sold in particular under the trade name "Parsol 1789" by Hoffmann-LaRoche), or isopropyl dibenzoylmethane, cinnamic derivatives, in particular ethylhexyl methoxycinnamate (sold in particular under the trade name "Parsol MCX" by Hoffmann-LaRoche), isopropyl methoxycinnamate, isoamyl methoxycinnamate (sold under the trade name "Neo Heliopan E 1000" by Haarmann and Reimer), cinoxate, DEA methoxycinnamate, diisopropyl methyl cinnamate, or glyceryl ethylhexanoate dimethoxycinnamate, β,β-diphenylacrylate derivatives, in particular octocrylene (sold in particular under the trade name "Uvinul N539" by BASF) or etocrylene (sold in particular under the trade name "Uvinul N35" by BASF), benzophenone, in particular benzophenone-1 (sold under the trade name "Uvinul 400" by BASF), benzophenone-2 (sold under the trade name "Uvinul D50" by BASF), benzophenone-3 or oxybenzone (sold under the trade name "Uvinul M40" by BASF), benzophenone-4 (sold under the trade name "Uvinul MS40" by BASF), benzophenone-5, benzophenone-6 (sold under the trade name "Helisorb 11" by Norquay), benzophenone-8 (sold under the trade name "Spectra-Sorb UV-24" by American Cyanamid), benzophenone-9 (sold under the trade name "Uvinul DS-49" by BASF), benzophenone-12, or n-hexyl 2-(4-d iethylamino-2-hydroxybenzoyl)benzoate, benzylidene camphor derivatives, in particular 3-benzylidene camphor (manufactured under the name "Mexoryl SD" by Chimex), 4-methylbenzylidene camphor (sold under the name "Eusolex 6300" by Merck), benzylidene camphor sulphonic acid (manufactured under the name "Mexoryl SL" by Chimex), camphor benzalkonium methosulphate (manufactured under the name "Mexoryl SO" by Chimex), terephthalylidene dicamphor sulphonic acid (manufactured under the name "Mexoryl SX" by Chimex), or polyacrylamidomethyl benzylidene camphor (manufactured under the name "Mesoryl SW" by Chimex), benzimidazole derivatives, in particular phenylbenzimidazole sulphonic acid (sold in particular under the trade name "Eusolex 232" by Merck), or disodium phenyl dibenzimidazole tetrasulphonate (sold under the trade name "Neo Heliopan AP" by Haarmann and Reimer), triazine derivatives, in particular anisotriazine (sold under the trade name "Tinosorb S" by Ciba Specialty Chemicals), ethylhexyl triazone (sold in particular under the trade name "Uvinul T150" by BASF), diethylhexyl butamido triazone (sold under the trade name "Uvasorb HEB" by Sigma 3V) or 2,4,6-tris(diisobutyl 4'-amino-benzalmalonate)-s-triazine, benzotriazole derivatives, in particular drometrizole trisiloxane (sold under the name "Silatrizole" by Rhodia Chimie) or methylene bisbenzotriazolyl tetramethylbutylphenol (sold in the solid form under the trade name "Mixxim BB/100" by Fairmount Chemical or in the micronized form in aqueous dispersion under the trade name "Tinosorb M" by Ciba Specialty Chemicals), anthranilic derivatives, in particular menthyl anthranilate (sold under the trade name "Neo Heliopan MA" by Haarmann and Reimer), imidazoline derivatives, in particular ethylhexyl dimethoxybenzylidene dioxoimidazoline propionate, benzalmalonate derivatives, in particular polyorganosiloxane comprising benzalmalonate functional groups (sold under the trade name "Parsol SLX" by Hoffmann-LaRoche), 4,4-diarylbutadiene derivatives, in particular 1,1'-dicarboxy (2,2'-dimethylpropyl)-4,4-diphenylbutadiene, and their mixtures.

The organic photoprotective agents which are more particularly preferred are chosen from ethylhexyl salicylate, ethylhexyl methoxycinnamate, octocrylene, phenylbenzimidazole sulphonic acid, benzophenone-3, benzophenone-4, benzophenone-5, 4-methylbenzylidene camphor, terephthalylidene dicamphor sulphonic acid, disodium phenyl dibenzimidazole tetrasulphonate, 2,4,6-tris(diisobutyl 4'-aminobenzalmalonate)-s-triazine, anisotriazine, ethylhexyl triazone, diethylhexyl butamido triazone, methylene bisbenzotriazolyl tetramethylbutylphenol, drometrizole trisiloxane, 1,1'-dicarboxy (2,2'-dimethyl-propyl)-4,4-diphenylbutadiene, and their mixtures.

The inorganic photoprotective agents are chosen from pigments or alternatively nanopigments (mean size of the primary particles: generally between 5 nm and 100 nm, preferably between 10 nm and 50 nm) formed from coated or uncoated metal oxides, such as, for example, titanium oxide (amorphous or crystalline in the rutile and/or anatase form), iron oxide, zinc oxide, zirconium oxide or cerium oxide nanopigments, which are all UV photoprotective agents well known per se. Conventional coating agents are, furthermore, alumina and/or aluminium stearate. Such nanopigments formed from coated or uncoated metal oxides are disclosed in particular in Patent Applications EP 518 772 and EP 518 773.

The photoprotective agents are generally present in the compositions according to the invention in proportions ranging from 0.1 to 20% by weight with respect to the total weight of the composition and preferably ranging from 0.2 to 15% by weight with respect to the total weight of the composition.

The composition according to the invention can be applied to the skin, hair, including body hair, eyelashes, nails or lips, depending on the use for which it is intended. It can thus be used in a cosmetic treatment process for the skin, comprising the application of the composition according to the invention to the skin.

In an alternative form, the composition according to the invention can be used for the manufacture of a dermatological preparation.

The examples which follow serve to illustrate the invention without, however, exhibiting a limiting nature. The compounds are, depending on the situation, cited according to chemical names or according to CTFA (International Cosmetic Ingredient Dictionary and Handbook) names.

EXAMPLES

Example 1

Accelerated Storage Test

The aim of this test is to study the decomposition of an oxidation-sensitive hydrophilic active principle after storing for two months at 45° C. Various solutions were prepared and their compositions are collated in the following table:

TABLE I

| Compositions (in water) | Solution A (Control) | Solution B | Solution C | Solution D |
|---|---|---|---|---|
| Ascorbic acid | 15% | 15% | 15% | 15% |
| Polymer 1 | — | 1% | — | — |
| Polymer 2 | — | — | 1% | — |
| Polymer 3 | — | — | — | 1% |

All the solutions are brought to pH 6 with 8.9 mol/l KOH.
The percentages of the polymers are given as active material.
Polymer 1: Vinylpyrrolidone/vinylimidazole (50/50) copolymer sold under the reference Luvitec VPI 55K72W of BASF (Weight-average molecular mass $1.2 \times 10^6$).
Polymer 2: Vinylpyrrolidone/vinylimidazole (50/50) copolymer sold under the reference Luvitec VPI 55K18P of BASF (Weight-average molecular mass 10000).
Polymer 3: Polyvinylpyrrolidone sold under the reference Kollidon 12PF of BASF (Weight-average molecular mass 3000).

The degree of decomposition measured is given by the ratio:

$$(C_0 - C_{2\ months})/C_0$$

with $C_0$ concentration of ascorbic acid at t=0 and $C_{2\ months}$ the concentration of ascorbic acid at t=2 months, under the conditions indicated in the above table. The concentration of ascorbic acid is determined by the HPLC technique (LaChrom Merck system). The analytical conditions are as follows:
Column: Lichrosphere100 RP18 (250 mm)
Eluent: 0.1M phosphate buffer, pH 2.1
Flow rate: 1 ml/min
Detection at 257 nm
Dilution of the sample such that the concentration of ascorbic acid is between 0.05 and 1 mg/ml.

The results obtained are collated in the following Table II:

TABLE II

| | Degree of decomposition after 2 months at 45° C. (in %) | |
|---|---|---|
| | under air, amber glass bottle | under nitrogen, aluminium flask |
| Solution A | 43 | 19.4 |
| Solution B | 10.8 | 1 |
| Solution C | 23.4 | 4.5 |
| Solution D | 35.8 | 15.7 |

It is found, from Table II, that the stability of ascorbic acid is improved in the presence of Polymer 1 and Polymer 2 of the invention, even in the presence of atmospheric oxygen, in comparison with the control. It is also found that the N-vinylpyrrolidone homopolymer alone is not sufficient to effectively stabilize the ascorbic acid solution. Preferred invention results for this test using ascorbic acid as above are 30 or below in air, including 25, 20, 15, 10, 5, etc. and less than or equal to 10 in nitrogen including 8, 5, etc. General degrees of decomposition after two months in air at 45° C. preferably are less than or equal to 25%, including 20, 15, 10, 5%, etc. and all intervening values as if written out. As the polymers mentioned are hydrophilic, it will be sufficient to add them to an aqueous ascorbic acid solution to stabilize the ascorbic acid.

Example 2

Fluid W/O Emulsion

The following composition is prepared in a way conventional to a person skilled in the art.

| Phase A: | |
|---|---|
| Cetyl dimethicone copolyol | 1.5 g |
| Polyglyceryl-4 isostearate | 0.5 g |
| Squalene | 3.7 g |
| Isohexadecane | 7.95 g |
| Polydimethylsiloxane | 4 g |
| Apricot oil | 2.25 g |
| Phase B: | |
| Ascorbic acid | 5 g |
| 50% Potassium hydroxide | 3 g |
| Vinylpyrrolidone/vinylimidazole copolymer (Luvitec VPI55K72W from BASF) | 3.3 g |
| Glycerol | 5 g |
| Preservatives | 0.4 g |
| Water | 60.4 g |
| Nylon-12 powder | 3 g |

A fluid is obtained which is soft on application, with good stability of the ascorbic acid.

Example 3

Fluid W/O Emulsion for the Radiance of the Complexion

The following composition is prepared in a way conventional to a person skilled in the art.

Phase A:

| | |
|---|---|
| Ethanoldiethonium polyisobutenyl triethyl-aminosuccinate (and) diethyl ethanolamine (Lubrizol LZ 5603) | 2 g |
| Isohexadecane | 8 g |
| Hydrogenated polyisobutylene | 3.7 g |
| Apricot oil | 6.4 g |

Phase B:

| | |
|---|---|
| Ascorbic acid | 5 g |
| 50% Potassium hydroxide | 3 g |
| Vinylpyrrolidone/vinylimidazole copolymer (Luvitec VPI55K72W from BASF) | 3.3 g |
| Glycerol | 5 g |
| Preservatives | 0.4 g |
| Water | 61.2 g |
| Nylon-12 powder | 2 g |

A care cream for the skin is obtained, which cream is soft on application, with good stability of the ascorbic acid.

Example 4

Fluid W/O Emulsion

The following composition is prepared in a way conventional to a person skilled in the art.

Phase A:

| | |
|---|---|
| Isostearyl diglyceryl succinate | 4 g |
| Octyldodecanol | 4 g |
| Apricot oil | 8 g |
| Cyclomethicone | 12 g |
| Synthetic ceramide | 0.1 g |
| Silicone gum | 6 g |

Phase B:

| | |
|---|---|
| Ascorbic acid | 5 g |
| 50% Potassium hydroxide | 3.07 g |
| Vinylpyrrolidone/vinylimidazole copolymer (Luvitec VPI55K72W from BASF) | 1 g |
| Glycerol | 2 g |
| Aluminium starch octenylsuccinate | 0.3 g |
| Preservatives | 0.5 g |
| Demineralized water | 54.03 g |

A care cream for the skin is obtained, which cream is pliable and soft on application, with good stability of the ascorbic acid.

Example 5

O/W Face Cream

The following composition is prepared in a way conventional to a person skilled in the art.

Phase A:

| | |
|---|---|
| Glyceryl stearate and PEG-100 stearate | 2.1 g |
| Polysorbate 60 | 0.9 g |
| Cetyl alcohol | 2.6 g |
| Hydrogenated polyisobutene | 12 g |
| Cyclomethicone | 8 g |

Phase B:

| | |
|---|---|
| Demineralized water | 59.23 g |
| Glycerol | 2 g |
| Ascorbic acid | 5 g |
| 50% Potassium hydroxide | 3.07 g |
| Vinylpyrrolidone/vinylimidazole copolymer (Luvitec VPI55K72W from BASF) | 1 g |
| Xanthan gum | 0.1 g |
| Carbomer | 0.4 g |

Phase C:

| | |
|---|---|
| Triethanolamine | 0.3 g |
| Demineralized water | 3 g |
| Preservative | 0.3 g |

A care cream for the skin is obtained, which cream is rich and soft on application, with good stability of the ascorbic acid.

Example 6

W/O/W Multiple Emulsion

The following composition is prepared in a way conventional to a person skilled in the art.

Primary emulsion

Phase A:

| | |
|---|---|
| Polyglyceryl-4 isostearate and cetyl dimethicone copolyol and hexyl laurate | 3.5 g |
| Cyclopentasiloxane | 16.5 g |
| Dimethicone (silicone gum) | 4 g |

Phase B:

| | |
|---|---|
| Demineralized water | 46.27 g |
| Ascorbic acid | 15 g |
| 50% Potassium hydroxide | 9.33 g |
| Vinylpyrrolidone/vinylimidazole copolymer (Luvitec VPI55K72W from BASF) | 3.3 g |
| Glycerol | 2 g |
| Pentasodium ethylenediaminetetramethylene-phosphonate (33% aqueous solution) | 0.1 g |

Multiple emulsion

Phase A:

| | |
|---|---|
| Primary emulsion | 20 g |
| Cyclopentasiloxane | 5 g |
| Apricot kernel oil | 5 g |

Phase B:

| | |
|---|---|
| Ammonium polyacryloyldimethyl taurate | 0.4 g |
| Acrylates/$C_{10-30}$ alkyl acrylate crosspolymer | 0.6 g |
| Demineralized water | 35.7 g |
| Preservative | 1 g |

Phase C:

| | |
|---|---|
| Demineralized water | 5.7 g |
| Triethanolamine | 0.7 g |

Phase D:

| | |
|---|---|
| Ammonium polyacryloyldimethyl taurate | 0.6 g |
| Demineralized water | 25.3 g |

A white and fresh cream is obtained which confers good stability on ascorbic acid and is capable of being applied to the skin.

Example 7

Ascorbic Acid Microcapsules

A 15% by weight aqueous ascorbic acid solution, at pH 6, comprising 3.3 g of vinylpyrrolidone/vinylimidazole copolymer (Luvitec VPI55K72W® from BASF), is prepared. 5 ml of this solution are emulsified in 50 ml of methylene chloride comprising 5% of cellulose acetate-propionate (CAP-482-0.5®, Eastman Chemical) for 5 min using a homogenizer of rotor-stator type while maintaining the temperature below 25° C. This primary emulsion is subsequently dispersed in 500 ml of an aqueous solution comprising 1% of polyvinyl alcohol (Airvol 203®, Air Products) and 7% of sodium chloride for 20 min at ambient temperature using a Moritz disperser.

The solvent of the suspension is subsequently evaporated for 5 hours at 40° C. at a pressure of 75 kPa using a rotary evaporator (Büchi B-480).

A dispersion of microcapsules, the mean size of which is 20 μm, with a degree of encapsulation of 85% and a manufacturing yield of 100%, is obtained.

Example 8

Day Cream Comprising the Microcapsules According to Example 7

| Phase A: | |
| --- | --- |
| Cetyl alcohol | 4 g |
| Sorbitan tristearate | 0.9 g |
| Polyethylene glycol stearate | 2 g |
| Glyceryl stearate | 3 g |
| Myristyl myristate | 2 g |
| Octyl palmitate | 4.5 g |
| Parsol MCX ® (sold by Hoffmann-LaRoche) | 3 g |
| Cyclopentasiloxane | 5 g |
| Preservative | 0.1 g |
| Phase B: | |
| Demineralized water | 60.3 g |
| Preservative | 0.15 g |
| Sequestering agent | 0.05 g |
| Phase C: | |
| Powder formed from microcapsules according to Example 7 | 15 g |

Example 9

W/O Cream

The following composition is prepared in a way conventional to a person skilled in the art.

| | |
| --- | --- |
| Water | 21.05 g |
| Phenoxyethanol | 0.5 g |
| Methyl paraben | 0.3 g |
| Water | 71.3 g |
| Kojic acid | 1 g |

-continued

| | |
| --- | --- |
| Vinylpyrrolidone/vinylimidazole copolymer | 0.5 g |
| Biosaccharide Gum-1 | 2 g |
| Polysorbate 20 | 1 g |
| Cyclopentasiloxane (and) dimethicone copolyol | 10 g |
| Cyclopentasiloxane | 8 g |
| Dimethicone (and) dimethicone/vinyl dimethicone crosspolymer | 3 g |
| Tocopherol (and) glycine soya (soybean) oil | 0.4 g |
| Polyacrylamide (and) $C_{13-14}$ isoparaffin (and) laureth-7 | 2 g |

A care cream for the skin is obtained, with good stability of the ascorbic acid.

Example 10

W/O Gel

The following composition is prepared in a way conventional to a person skilled in the art.

| | |
| --- | --- |
| Cyclopentasiloxane (and) dimethicone copolyol | 17.5 g |
| Sodium methylparaben | 0.3 g |
| Chlorphenesin | 0.25 g |
| Water | 81.2 g |
| Phloroglucinol | 0.5 g |
| Vinylpyrrolidone/vinylimidazole copolymer | 0.25 g |

A gel for the skin is obtained, with good stability of the ascorbic acid.

The above description of the invention, as explained and illustrated by Examples, enables one of ordinary skill in the art to make and use a composition comprising, preferably in a physiologically acceptable medium comprising an aqueous phase, at least one oxidation-sensitive hydrophilic active principle and at least one non-crosslinked N-vinylimidazole polymer or copolymer, the active principle and the polymer or copolymer both being in the aqueous phase. In addition, one of ordinary skill is enabled to use a non-crosslinked N-vinylimidazole polymer or copolymer to stabilize an oxidation-sensitive hydrophilic active principle in an aqueous medium.

French patent application 0115375 is incorporated herein by reference, as are all documents, references, texts, standards, applications, patents, etc., mentioned above.

Also incorporated herein by reference are the following U.S. applications, all filed Nov. 27, 2002, where the present application is listed for information only:

U.S. Ser. No. 10/304,860
U.S. Ser. No. 10/304,861
U.S. Ser. No. 10/305,115
U.S. Ser. No. 10/304,862
U.S. Ser. No. 10/305,114

The invention claimed is:

1. A composition comprising: a physiologically acceptable medium comprising an aqueous phase; at least one oxidation-sensitive hydrophilic active principle, wherein the hydrophilic active principle is selected from the group consisting of ascorbic acid, 5,6-di-O-dimethylsilylascorbate, dl-α-tocopheryl di-ascorbyl phosphate potassium salt, magnesium ascorbyl phosphate, sodium ascorbyl phosphate phloroglucinol, kojic acid, and mixtures thereof; and at least one non-crosslinked N-vinylimidazole/N-vinylpyrrolidone copolymer, the at least one active principle and the at least one non-crosslinked-N-vinylimidazole/N-vinylpyrrolidone copolymer both being present in the aqueous phase, wherein the copolymer is present in concentration of between 0.1 and 5% by weight of the aqueous phase and wherein no more than 30% of the oxidation-sensitive hydrophilic active principle in the composition is decomposed after 2 months at 45° C.

2. A composition according to claim 1, wherein the oxidation-sensitive hydrophilic active principle is ascorbic acid.

3. A composition according to claim 1, comprising a non-crosslinked copolymer selected from the group consisting of a vinylpyrrolidone/vinylimidazole (50/50) copolymer having a weight-average molar mass of 1 200 000 and a vinylpyrrolidone/vinylimidazole (50/50) copolymer having a weight-average molar mass of 10 000.

4. A composition according to claim 1, wherein the molar ratio of the N-vinylimidazole unit equivalent to the oxidation-sensitive hydrophilic active principle is from 0.004 to 16.

5. A composition according to claim 4, wherein the molar ratio of the N-vinylimidazole unit equivalent to the oxidation-sensitive hydrophilic active principle is from 0.01 to 1.

6. A composition according to claim 1, wherein the copolymer is present in a concentration of between 0.1 and 2% by weight of the aqueous phase.

7. A composition according to claim 1, wherein the copolymer has a molar fraction of N-vinylimidazole units of from 0.1 to 1.

8. A composition according to claim 7, wherein the copolymer has a molar fraction of N-vinylimidazole units of from 0.4 to 0.9.

9. A composition according to claim 1, wherein the active priciniple is selected from the group consisting of 5,6-di-O-dimethylsilylascorbate, dl-α-tocopheryl di-ascorbyl phosphate potassium salt, magnesium ascorbyl phosphate, sodium ascorbyl phosphate phioroglucinol, and mixtures thereof.

10. A method of stabilizing an oxidation-sensitive hydrophilic active principle in an aqueous medium, comprising adding thereto a stabilizing amount of a non-crosslinked N-vinylimidazole/N-vinylpyrrolidone copolymer, wherein the hydrophilic active principle is selected from the group consisting of ascorbic acid, 5,6-di-O-dimethylsilylascorbate, dl-a-tocopheryl di-ascorbyl phosphate potassium salt, magnesium ascorbyl phosphate, sodium ascorbyl phosphate phioroglucinol, kojic acid, and mixtures thereof.

11. The method according to claim 10, wherein the non-crosslinked copolymer is selected from the group consisting of a vinylpyrrolidone/vinylimidazole (50/50) copolymer having a weight-average molar mass of 1 200 000 and a vinylpyrrolidone/vinylimidazole (50/50) copolymer having a weight-average molar mass of 10 000.

12. The method according to claim 10, wherein the oxidation-sensitive hydrophilic active principle is ascorbic acid.

13. The composition according to claim 1, wherein no more than 25% of the oxidation-sensitive hydrophilic active principle in the composition is decomposed after 2 months at 45° C.

14. method of treating skin comprising applying the composition according to claim 1 to skin.

* * * * *

UNITED STATES PATENT AND TRADEMARK OFFICE
CERTIFICATE OF CORRECTION

PATENT NO. : 7,560,493 B2  
APPLICATION NO. : 10/304860  
DATED : July 14, 2009  
INVENTOR(S) : Bruno Biatry et al.

Page 1 of 1

It is certified that error appears in the above-identified patent and that said Letters Patent is hereby corrected as shown below:

Column 16, line 3, "phioroglucinol" should read --phloroglucinol--;
        line 13, "phioroglucinol" should read --phloroglucinol--.

Signed and Sealed this

Thirteenth Day of October, 2009

David J. Kappos
*Director of the United States Patent and Trademark Office*